United States Patent
Morita et al.

(10) Patent No.: US 12,297,473 B2
(45) Date of Patent: May 13, 2025

(54) PRODUCTION OF MONOACYL MEL

(71) Applicants: NATIONAL INSTITUTE OF ADVANCED INDUSTRIAL SCIENCE AND TECHNOLOGY, Tokyo (JP); TOYOBO CO., LTD., Osaka (JP)

(72) Inventors: Tomotake Morita, Tsukuba (JP); Azusa Saika, Tsukuba (JP); Tokuma Fukuoka, Tsukuba (JP); Dai Kitamoto, Tsukuba (JP); Tomohiro Sugahara, Tsuruga (JP); Shuhei Yamamoto, Osaka (JP); Atsushi Sogabe, Osaka (JP)

(73) Assignees: NATIONAL INSTITUTE OF ADVANCED INDUSTRIAL SCIENCE AND TECHNOLOGY, Tokyo (JP); TOYOBO CO., LTD., Osaka (JP)

( * ) Notice: Subject to any disclaimer, the term of this patent is extended or adjusted under 35 U.S.C. 154(b) by 614 days.

(21) Appl. No.: 17/635,991

(22) PCT Filed: Aug. 24, 2020

(86) PCT No.: PCT/JP2020/031766
§ 371 (c)(1),
(2) Date: Feb. 16, 2022

(87) PCT Pub. No.: WO2021/039686
PCT Pub. Date: Mar. 4, 2021

(65) Prior Publication Data
US 2022/0275414 A1 Sep. 1, 2022

(30) Foreign Application Priority Data
Aug. 26, 2019 (JP) ................ 2019-153509

(51) Int. Cl.
*C12P 19/44* (2006.01)
(52) U.S. Cl.
CPC .................. *C12P 19/44* (2013.01)
(58) Field of Classification Search
CPC ....... C12P 19/44; A61K 8/99; A61K 2800/10; A61K 8/60; A61K 8/06; A61Q 19/00
See application file for complete search history.

(56) References Cited

FOREIGN PATENT DOCUMENTS

| CN | 103589764 A | 2/2014 |
|---|---|---|
| JP | 2007-185142 A | 7/2007 |
| JP | 2011-182660 A | 9/2011 |
| JP | 2011-182740 A | 9/2011 |
| JP | 2016-191438 A | 11/2016 |
| JP | 2018-052874 A | 4/2018 |
| JP | 2018-113946 A | 7/2018 |
| WO | WO 2000/029604 A1 | 5/2000 |
| WO | WO 2012/146937 A1 | 11/2012 |
| WO | WO 2014/109360 A1 | 7/2014 |
| WO | WO 2017/208791 A1 | 12/2017 |
| WO | WO 2021/010264 A1 | 1/2021 |

OTHER PUBLICATIONS

Huang et al., Using non-ionic surfactant as an accelerator to increase extracellular lipid production by oleaginous yeast *Cryptococcus curvatus* MUCL 29819, Bioresource Technology, vol. 274, 2019,pp. 272-280, ISSN 0960-8524, doi.org/10.101 (Year: published online 2018) (Year: 2018).*
Tomano et al., High-efficiency extracellular release of free fatty acids from *Aspergillus oryzae* using non-ionic surfactants, Journal of Biotechnology, vol. 248, 2017,pp. 9-14; doi.org/10.1016/j.jbiotec. 2017.03.002. (Year: 2017).*
Avis et al., "Usefulness of Heterologous Promoters in the *Pseudozyma flocculosa* Gene Expression System," *Biosci. Biotechnol. Biochem.*, 72(2): 456-462 (2008).
Faria et al., "Production of Glycolipid Biosurfactants, Mannosylerythritol Lipids, from Pentoses and D-Glucose/D-Xylose Mixtures by *Pseudozyma* Yeast Strains," *Process Biochemistry*, 49(11): 1790-1799 (2014).
Neveu et al., "Cloning of the Glyceraldehyde-3-Phosphate Dehydrogenase Gene from *Pseudozyma flocculosa* and Functionality of its Promoter in two *Pseudozyma* Species," *Antonie van Leeuwenhoek*, 92(2): 245-255 (2007).
European Patent Office, Extended European Search Report in European Patent Application No. 20841145.4 (Jul. 7, 2023).
Saika et al., "Biosynthesis of Mono-Acylated Mannosylerythritol Lipid in an Acyltransferase Gene-Disrupted Mutant of *Pseudozyma tsukubaensis*," *Appl. Microbiol. Biotechnol.*, 102(4): 1759-1767 (2018).
European Patent Office, Extended European Search Report in European Patent Application No. 20856771.9 (Jul. 14, 2023).
Fukuoka et al., "Structural characterization and surface-active properties of a new glycolipid biosurfactant, mono-acylated mannosylerythritol lipid, produced from glucose by *Pseudozyma antarctica*," *Appl. Microbiol. Biotechnol.*, 76(4): 801-810 (2007).
Hewald et al., "Identification of a Gene Cluster for Biosynthesis of Mannosylerythritol Lipids in the Basidiomycetous Fungus *Ustilago maydis*," *Appl. Environ. Microbiol.*, 72(8): 5469-5477 (2006).
Kawashima et al., "Extracellular Production of a Mannosylerythritol by a Mutant of *Candida* sp. from n-Alkanes and Triacylglycerols," *J. Ferment. Technol.*, 61(2): 143-149 (1983).
Kim et al., "A glycolipid biosurfactant produced from *Candida* sp. SY16," *Abstracts of the Year 1998 Convention of the Society for Fermentation and Bioengineering*, Abstract 934, p. 195 (1998).

(Continued)

*Primary Examiner* — Kade Ariani
(74) *Attorney, Agent, or Firm* — Leydig, Voit & Mayer, Ltd.

(57) ABSTRACT

Provided is a method for efficiently producing a monoacyl MEL. The method comprises culturing a monoacyl-MEL-producing microorganism in the presence of a surfactant.

8 Claims, 5 Drawing Sheets

Specification includes a Sequence Listing.

(56) References Cited

OTHER PUBLICATIONS

Kitamoto et al., "Extracellular Accumulation of Mannosylerythritol Lipids by a Strain of *Candida antarctica*," *Agric. Biol. Chem.*, 54(1): 31-36 (1990).

Kitamoto et al., "Production of Mannosylerythritol Lipids by *Candida antarctica* from Vegetable Oils," *Agric. Biol. Chem.*, 54(1): 37-40 (1990).

Kitamoto et al., "Production of Mannosylerythritol Lipids as Biosurfactants by Resting Cells of *Candida antarctica*," *Biotechnol. Lett.*, 14(4): 305-310 (1992).

Morita et al., "Isolation of basidiomycetous yeast *Pseudozyma tsukubaensis* and production of glycolipid biosurfactant, a diastereomer type of mannosylerythritol lipid-B," *Appl. Microbiol. Biotechnol.*, 88(3): 679-688 (2010).

Nakahara et al., "Induction and Characterization of Mutants Assimilability of n-Alkanes in Shake Cultures from a Strain of *Candida* sp.," *J. Ferment. Technol.*, 61(1): 19-23 (1983).

Saika et al., "Enhanced production of a diastereomer type of mannosylerythritol lipid-B by the basidiomycetous yeast *Pseudozyma tsukubaensis* expressing lipase genes from *Pseudozyma antarctica*," *Appl. Microbiol. Biotechnol.*, 101(23-24): 8345-8352 (2017).

Saika et al., "Identification of the gene PIMAT1 encoding acetyltransferase from the diastereomer type of mannosylerythritol lipid-B producer *Pseudozyma tsukubaensis*," *J. Biosci. Bioeng.*, 126(6): 676-681 (2018).

Saika et al., "Deficiency of biodegradable plastic-degrading enzyme production in a gene-deletion mutant of phyllosphere yeast, *Pseudozyma antarctica* defective in mannoosylerythritol lipid biosynthesis," *AMB Express*, 9(1): 100 (2019).

Japanese Patent Office, International Search Report in International Patent Application No. PCT/JP2020/026760 (Sep. 1, 2020).

Japanese Patent Office, International Search Report in International Patent Application No. PCT/JP2020/031766 (Oct. 20, 2020).

Chica et al., "Semi-rational Approaches to Engineering Enzyme Activity: Combining the Benefits of Directed Evolution and Rational Design," *Curr. Opin. Biotechnol.*, 16(4): 378-384 (2005).

Singh et al., "Protein Engineering Approaches in the Post-Genomic Era," *Curr. Protein Pep. Sci.*, 18(4): 1-11 (2017).

Neveu et al., "The *Pseudozyma flocculosa* Actin Promoter Allows the Strong Expression of a Recombinant Protein in the *Pseudozyma Species*," *Appl. Microbiol. Biotechnol.*, 74(6): 1300-1307 (2007).

Japan Patent Office, Office Action in Japanese Patent Application No. 2021-533006 (Mar. 12, 2024).

U.S. Appl. No. 17/626,475, filed Jan. 11, 2022.

Saika et al., "Tailor-made mannosylerythritol lipids: current state and perspectives," *Appl. Microbiol. Biotechnol.*, 102: 6877-6884 (2018).

Saika et al., "A putative transporter gene PtMMF1-deleted strain produces mono-acylated mannosylerythritol lipids in *Pseudozyma tsukubaensis*," *Appl. Microbiol. Biotechnol.*, 104: 10105-10117 (2020).

\* cited by examiner (a)

(b)

(a)

(b)

(a)

◀ Monoacyl MEL (b)

0.01%  ◀ Monoacyl MEL 0.01%  ◀ Monoacyl MEL

PRODUCTION OF MONOACYL MEL

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 14,544 bytes ASCII (Text) file named "759572Sequence-Listing.txt," created Feb. 14, 2022.

TECHNICAL FIELD

A technique for producing a monoacyl MEL using a microorganism is disclosed.

BACKGROUND ART

Biosurfactants are natural surfactants produced by microorganisms. Biosurfactants are highly biodegradable, have a low environmental impact, and possess a variety of beneficial physiological functions. Therefore, their use in the food industry, cosmetics industry, pharmaceutical industry, chemical industry, environmental industry, and like industrial fields is significant in realizing an environmentally harmonious society.

Biosurfactants can be classified into five groups: glycolipid biosurfactants, acyl peptide biosurfactants, phospholipid biosurfactants, fatty acid biosurfactants, and polymeric biosurfactants. Among these, glycolipid surfactants have been the most well studied. Known as such glycolipid biosurfactants are mannosylerythritol lipids (hereinafter also referred to as MELs) wherein a fatty acid is ester-linked to mannosylerythritol wherein erythritol is glycosidically linked to mannose (hereinafter also referred to as ME); rhamnolipids, ustilagic acids, trehalose lipids, sophorose lipids, and the like.

MELs have various structures that are different in positions and number of fatty acid residues and acetyl groups that are bound. FIG. 1 shows a structural formula of a MEL wherein $R_1$ to $R_5$ each represent a hydrogen atom, an acetyl group, or a $C_{3-18}$ fatty acid residue. The structure in which $R_1$ and $R_2$ are fatty acid residues and $R_3$ and $R_4$ are acetyl groups is defined as MEL-A. The structure in which $R_3$ is a hydrogen atom and $R_4$ is an acetyl group is defined as MEL-B. The structure in which $R_3$ is an acetyl group and $R_4$ is a hydrogen atom is defined as MEL-C. The structure in which $R_3$ and $R_4$ are hydrogen atoms is defined as MEL-D. As shown in FIGS. 2(a) and 2(b), the structure of the obtained ME is different depending on whether the hydroxymethyl group of erythritol bound to mannose is derived from the carbon at 1-position or the carbon at 4-position. The MEL that has, as a sugar backbone, 4-O-β-D-mannopyranosyl-erythritol shown in FIG. 2(a) is referred to as 4-O-β-D-MEL. *Pseudozyma tsukubaensis* is known to produce 1-O-β-D-MEL-B, which has, as a sugar backbone, 1-O-β-D-mannopyranosyl-erythritol shown in FIG. 2(b). The 1-O-β-MEL-B is characterized by having enhanced hydrating properties and high vesicle-forming ability as compared to 4-O-β-MEL-B, and is a promising biomaterial for skin care products etc.

It has been reported that when MEL-producing yeast is cultured using only glucose as a carbon source, monoacyl MELs (single-chain MEL), which are MELs shown in FIG. 1 wherein a fatty acid is bound to only $R_2$ and $R_1$, $R_3$, and $R_4$ are hydrogen atoms, can be produced (Non-patent Literature (NPL) 1). This monoacyl MEL has enhanced hydrophilicity as compared to conventional diacyl MELs (Non-patent Literature (NPL) 1).

The MEL biosynthetic pathway has already been reported. MEL is synthesized intracellularly by the reaction of glycosyltransferase, which binds mannose and erythritol; acyltransferase, which binds fatty acids; and acetyltransferase, which binds acetyl groups (Non-patent Literature (NPL) 2).

The present inventors found that deletion of the gene for acyltransferase from a microorganism capable of producing a biosurfactant yields monoacyl MELs with an aliphatic acyl group bound to only $R_1$ in the structural formula shown in FIG. 1 (Patent Literature (PTL) 1).

CITATION LIST

Patent Literature

PTL 1: Japanese Patent Application No. 2016-191438 (JP2018-52874A)

Non-Patent Literature

NPL 1: Fukuoka et al., Appl. Microbiol. Biotechnol. (2007) 76: 801-810.
NPL 2: Hewald et al., Appl. Environ. Microbiol. (2006) 72: 5469-5477

SUMMARY OF INVENTION

Technical Problem

One object to be achieved is efficient production of a monoacyl MEL.

Solution to Problem

As a result of intensive research to achieve the above object, it was found that monoacyl MEL production efficiency could be improved by adding a surfactant to a culture medium when monoacyl MEL-producing yeast is cultured. As a result of further research and consideration based on these findings, the inventions represented below are provided.

Item 1
  A method for producing a monoacyl MEL, comprising culturing a microorganism capable of producing the monoacyl MEL in the presence of a surfactant.
Item 2
  The method according to Item 1, wherein the surfactant is a nonionic surfactant.
Item 3
  The method according to Item 1 or 2, wherein the microorganism is a microorganism that belongs to the genus *Pseudozyma*.
Item 4
  The method according to any one of Items 1 to 3, wherein the microorganism is deficient in a gene encoding mannose acyltransferase.
Item 5
  The method according to any one of Items 1 to 4, further comprising extracting the monoacyl MEL using at least one member selected from the group consisting of methanol, ethanol, acetone, and mixtures thereof.

Item 6
An enhancer for enhancing monoacyl MEL production capacity of a microorganism capable of producing a monoacyl MEL, the enhancer comprising a surfactant.

Item 7
Use of a surfactant in enhancing monoacyl MEL production capacity of a microorganism capable of producing a monoacyl MEL.

Advantageous Effects of Invention

The monoacyl MEL efficiency can be enhanced.

DESCRIPTION OF EMBODIMENTS

Figure 1:
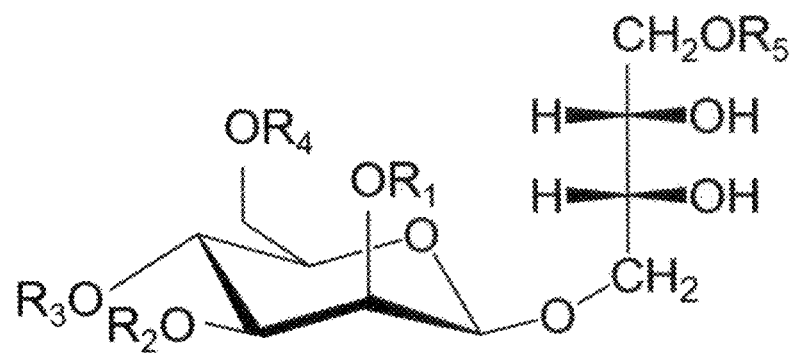
FIG. 1 shows the structure of MEL.
Figure 2:
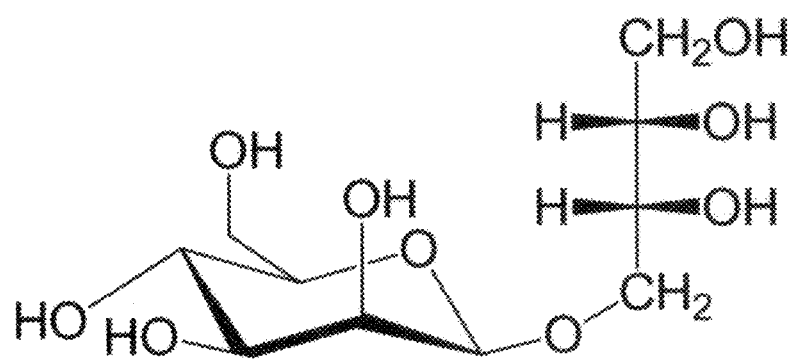
FIG. 2 shows the structures of 4-O-β-D-mannopyranosyl-erythritol (a) and 1-O-β-D-mannopyranosyl-erythritol (b).
Figure 2:
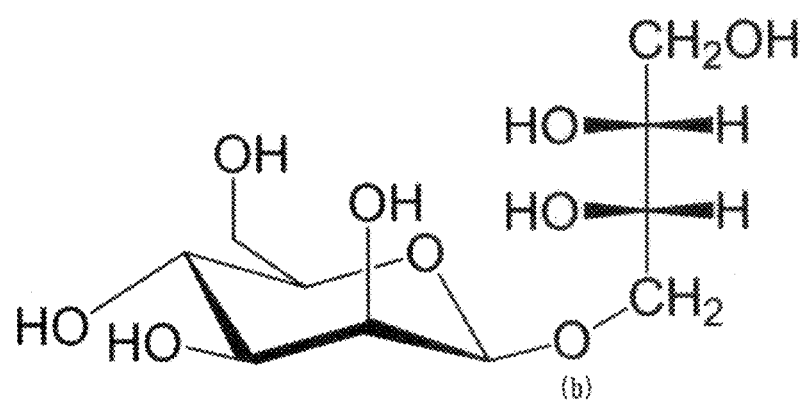

When a microorganism that produces a monoacyl MEL is to be cultured, the microorganism is preferably cultured in the presence of a surfactant. The type of surfactant is not particularly limited, and any surfactant can be used. For example, the surfactant can be a nonionic surfactant, an anionic surfactant, a cationic surfactant, or an amphoteric surfactant. In one embodiment, the surfactant is preferably a nonionic surfactant. Examples of nonionic surfactants include ether-based surfactants, ester-based surfactants, ester-ether-based surfactants, and the like. In one embodiment, the nonionic surfactant is preferably an ether-based surfactant. Examples of ether-based nonionic surfactants include polyoxyethylene-based surfactants (e.g., polyoxyethylene octylphenyl ether (Triton X-100), polyoxyethylene sorbitan monolaurate (Tween 20) and polyoxyethylene lauryl ether (BRIJ35)), block polymer-based surfactants (e.g., polyoxyethylene polyoxypropylene glycol and polyoxyethylene polyoxypropylene alkyl ether), MEL, sophorolipid, rhamnolipid, trehalose lipid, and the like. Such surfactants can be used singly, or in a combination of two or more. In one embodiment, the surfactant is preferably an anionic surfactant. Examples of anionic surfactants include carboxylic acid-based surfactant/ts (e.g., sodium octanoate, sodium decanoate, sodium laurate, sodium myristate, sodium palmitate, sodium stearate, etc.), sulfonic acid-based surfactants (e.g., sodium 1-hexanesulfonate, sodium 1-octanesulfonate, sodium 1-decanesulfonate, sodium 1-dodecanesulfonate, perfluorobutanesulfonic acid, sodium toluenesulfonate, etc.), and phosphoric acid ester surfactants (e.g., lauryl phosphate, sodium lauryl phosphate, potassium lauryl phosphate, etc.), and the like. Such surfactants can be used singly, or in a combination of two or more.

The mode of culturing a monoacyl MEL-producing microorganism in the presence of a surfactant is not particularly limited. For example, a surfactant can be added to a liquid medium, and a monoacyl MEL-producing microorganism can be cultured in the medium. The amount of surfactant added to the medium is not particularly limited, and can be appropriately selected in consideration of, for example, the type of surfactant, the kind of microorganism, and the type of medium. For example, the surfactant can be added to the medium at a concentration of 0.0001 mass % or more and 1 mass % or less, 0.001 mass % or more and 1 mass % or less, 0.0001 mass % or more and 0.1 mass % or less, 0.001 mass % or more and 0.1 mass % or less, 0.01 mass % or more and 0.1 mass % or less, 0.0001 mass % or more and 0.05 mass % or less, 0.001 mass % or more and 0.05 mass % or less, 0.0001 mass % or more and 0.01 mass % or less, or 0.001 mass % or more and 0.01 mass % or less.

Conventional ethyl acetate is not suitable as a solvent for extracting a monoacyl MEL from a culture broth. In one embodiment, a monoacyl MEL can be extracted by using methanol, ethanol, or acetone after freeze-drying the culture broth.

The type of microorganism that produces a monoacyl MEL is not limited. For example, microorganisms that produce monoacyl MELs described in PTL 1 can be used. The patent literature is incorporated herein by reference in its entirety. In one embodiment, the monoacyl MEL-producing microorganism is preferably a microorganism that belongs to the genus *Pseudozyma, Moesziomyces, Ustilago, Sporisorium, Melanopsichium,* or *Kurtzmanomyces*. Examples of preferred microorganisms that belong to the genus *Pseudozyma* include *Pseudozyma antarctica* (*Moesziomyces antarcticus*), *Pseudozyma parantarctica, Pseudozyma* rugulosa, *Pseudozyma* siamensis, *Pseudozyma* shanxiensis, *Pseudozyma* crassa, *Pseudozyma* churashimaensis, *Pseudozyma aphidis* (*Moesziomyces aphidis*), *Pseudozyma hubeiensis,* and *Pseudozyma tsukubaensis*. Examples of preferred microorganisms that belong to the genus *Moesziomyces* include *Moesziomyces antarcticus* and *Moesziomyces aphidis*. Examples of preferred microorganisms that belong to the genus *Ustilago* include *Ustilago hordei* and *Ustilago maydis*. Examples of preferred microorganisms that belong to the genus *Sporisorium* include *Sporisorium reilianum* and *Sporisorium scitamineum*. Examples of preferred microorganisms that belong to the genus *Melanopsichium* include *Melanopsichium pennsylvanicum*. Examples of preferred microorganisms that belong to the genus *Kurtzmanomyces* include *Kurtzmanomyces* sp. I-11. In one preferred embodiment, the MEL-producing microorganism is a microorganism of the genus *Pseudozyma*, more preferably a microorganism that belongs to *Pseudozyma tsukubaensis,* and more specifically *Pseudozyma tsukubaensis* 1E5 (JCM16987 strain), NBRC1940 (ATCC24555, CBS422.96, CBS6389, DBVPG6988, PYCC4855, JCM10324, MUCL29894, NCYC1510, NRLY-7792). Microorganisms that belong to *Pseudozyma tsukubaensis* are known to selectively produce 1-O-β-MEL-B.

In one embodiment, the monoacyl MEL-producing microorganism can be obtained by mutating a microorganism that produces a conventional MEL. Here, the conventional MEL is diacyl MEL. The type of mutation is not limited, and is preferably a mutation that disrupts a gene encoding an acyltransferase possessed by a MEL-producing microorganism. Gene disruption means that a protein encoded by a gene (e.g., an acyltransferase) ceases to function. The mode of disruption is not particularly limited. In one embodiment, the monoacyl MEL-producing microorganism can be obtained by disrupting a gene encoding an acyltransferase possessed by a MEL-producing microorganism. A MEL-producing microorganism generally has two kinds of mannose acyltransferases (MAC1 and MAC2). MAC1 and MAC2 are acyltransferases that catalyze the reaction of binding fatty acids to hydroxyl groups at the 2- and 3-positions of mannose. In order to produce a monoacyl MEL-producing microorganism, a gene encoding either MAC1 or MAC2 may be disrupted, or genes encoding MAC1 and MAC2 may both be disrupted. In one preferred embodiment, the gene encoding MAC2 is preferably disrupted.

The gene disruption can be performed by any method. For example, the gene disruption can be performed by introducing a mutation into the base sequence of the gene, disrupting or deleting the expression control region (promoter etc.) of the gene, or inhibiting the translation of a transcript of the gene. These can be performed, for example, by homologous recombination, transposon, transgene, post-transcriptional gene silencing, RNAi, nonsense mediated decay (NMD), ribozyme, antisense, miRNA (micro-RNA), siRNA (small interfering RNA), and like methods.

In one embodiment, the gene disruption is preferably performed by homologous recombination. Methods for disrupting genes by homologous recombination are well known. For example, disruption of the target gene by homologous recombination can be performed by a method comprising: creating a gene cassette in which a selection marker gene, such as a gene that complements drug resistance or nutrient requirements, is inserted into the ORF of the target gene; incorporating the gene cassette into an appropriate vector (e.g., a plasmid); and introducing the resulting vector into a host microorganism (e.g., a conventional MEL-producing microorganism) to insert a marker gene into the target gene by homologous recombination. A microorganism whose target gene has been disrupted can be selected based on the expression of the above marker gene.

The marker gene to be used in the homologous recombination method can be selection marker genes for transformants that are usually used in genetic engineering. Examples include genes that confer resistance to drugs, such as hygromycin, zeocin, kanamycin, chloramphenicol, and G418; and genes that complement nutrient requirements, such as uracil synthase, leucine synthase, adenine synthase, and lysine synthase.

In one embodiment, the target gene is preferably an MAC2 gene. Examples of representative MAC2 genes are as follows. SEQ ID NO: 1 is a nucleotide sequence encoding acyltransferase (PaMAC2) derived from *Pseudozyma antarctica* strain T34. SEQ ID NO: 2 is a nucleotide sequence encoding acyltransferase (PaMAC2) derived from *Pseudozyma antarctica* JCM10317. SEQ ID NO: 3 is a nucleotide sequence encoding acyltransferase (PhMAC2) derived from *Pseudozyma hubeiensis* SY62. SEQ ID NO: 4 is a nucleotide sequence encoding acyltransferase (PtMAC2) derived from *Pseudozyma tsukubaensis* NBRC1940. SEQ ID NO: 5 is a nucleotide sequence encoding an acyltransferase (PtMAC2) derived from *Pseudozyma tsukubaensis* strain 1E5. SEQ ID NO: 6 is a nucleotide sequence encoding acyltransferase (MAC2) derived from *Pseudozyma aphidis* DSM70725. Based on the information of these sequences, a vector for disrupting an acyltransferase gene can be constructed. *P. antarctica* T-34 is also referred to as "*Moesziomyces antarcticus* T-34." *P. aphidis* is also referred to as "*Moesziomyces aphidis*."

Examples of vectors for use when a microorganism of the genus *Pseudozyma* is used as a host include pUXV1 ATCC 77463, pUXV2 ATCC 77464, pUXV5 ATCC 77468, pUXV6 ATCC 77469, pUXV7 ATCC 77470, pUXV8 ATCC 77471, pUXV3 ATCC 77465, pU2X1 ATCC 77466, pU2X2 ATCC 77467, pTA2, pUXV1-neo, pPAX1-neo, pPAA1-neo (Appl. Microbiol. Biotechnol. (2016) 100: 3207-3217), pUC_neo, pUC$_T$_neo, and the like.

The transfection of the vector into a host cell can be performed by any method that can be suitably selected according to the host cell, the type of vector, etc. For example, the transfection of the vector can be performed by electroporation, the calcium phosphate co-precipitation method, lipofection, microinjection, the lithium acetate method, and the like.

The production of a monoacyl MEL by using a monoacyl-MEL-producing microorganism can be performed by any method. For example, a monoacyl MEL can be produced by culturing a monoacyl-MEL-producing microorganism in a medium suitable for culturing a MEL-producing microorganism. The medium to be used is not particularly limited. For example, a carbohydrate, such as glucose, sucrose, or blackstrap molasses is preferably used as a carbon raw material. In addition to, or in place of, a carbohydrate, a fat and/or an oil can also be used as a carbon source. The kind of fat and/or oil is not particularly limited. For example, vegetable fats and oils, fatty acids, or esters thereof are preferably added.

In one embodiment, adding vegetable fat and/or oil to the culture medium is preferred. The kind of vegetable oil is not particularly limited, and can be appropriately selected according to, for example, the type of MEL desired. Examples of vegetable fats and oils include soybean oil, olive oil, rapeseed oil, safflower oil, sesame oil, palm oil, sunflower oil, coconut oil, cocoa butter, castor oil, and the like. Examples of fatty acids include caprylic acid, capric acid, lauric acid, myristic acid, palmitic acid, stearic acid, oleic acid, linoleic acid, linolenic acid, arachidonic acid, behenic acid, nervonic acid, and the like. In one embodiment, a preferred fatty acid is oleic acid.

In one embodiment, the monoacyl-MEL-producing microorganism can be cultured in a medium containing only glucose as a carbon source. As a nitrogen source, a combination of an organic nitrogen source and an inorganic nitrogen source can be used. As the organic nitrogen source, for example, one member or a combination of two or more members selected from the group consisting of yeast extracts, malt extracts, peptone, polypeptone, corn steep liquor, casamino acid, and urea can be used.

As the inorganic nitrogen source, one member or a combination of two or more members selected from the group consisting of sodium nitrate, potassium nitrate, ammonium nitrate, ammonium sulfate, and ammonia can be used. In another embodiment, a method of producing a monoacyl MEL is provided, which comprises culturing a microorganism capable of producing the monoacyl MEL in a medium containing fatty acid and glycerin.

The amount of fatty acid and the amount of fat and/or oil are not particularly limited. For example, fatty acid and fat and/or oil can be added in such an amount as for each to achieve a concentration of 0.1 to 40 volume % in the medium.

The conditions for culturing the microorganism are not particularly limited. For example, culture can be performed at pH 5 to 8, preferably pH 6, and at a temperature of 20 to 35° C., preferably 22 to 28° C., for 3 to 7 days.

The extraction of a monoacyl MEL produced by a microorganism capable of producing the monoacyl MEL can be performed by any method. For example, the monoacyl MEL can be obtained by a method comprising centrifuging a culture broth or a disrupted cell suspension, collecting the obtained supernatant, adding an appropriate extraction solvent to the supernatant, collecting the extraction solvent layer, and optionally further performing purification as necessary. In one embodiment, the extraction solvent used for extracting the monoacyl MEL is preferably at least one member selected from the group consisting of methanol, ethanol, acetone, and mixtures thereof, from the viewpoint of extraction efficiency. Acetone is preferred from the viewpoint that it can efficiently separate a monoacyl MEL from hydrophilic impurities to obtain the monoacyl MEL.

As described above, the use of a surfactant can enhance the efficiency (capacity) of producing the monoacyl MEL by a microorganism, and also provide the monoacyl MEL more stably. Therefore, in one embodiment, a surfactant can be used as a promoter for promoting monoacyl MEL production by a monoacyl-MEL-producing microorganism. In another embodiment, a surfactant can be used to promote monoacyl MEL production by a monoacyl MEL-producing microorganism or stabilize monoacyl MEL production.

EXAMPLES

The present invention is described below in more detail with reference to Examples. However, the present invention is not limited to these Examples.
1. Materials
   Yeast cells used
   Monoacyl-MEL-producing strain: *Pseudozyma tsukubaensis* strain 1E5 (JCM16987) acyltransferase (PtMAC2) disrupted strain
   Surfactants
   MEL-B (purified *Pseudozyma tsukubaensis* culture)
   Tween 20 (produced by Sigma)
   Triton X-100 (produced by MP Biomedicals)
   BRIJ35 (produced by MP Biomedicals)
   Sodium laurate (produced by Fujifilm Wako Pure Chemicals Corporation)
   Media
   YM medium with glycerol: prepared by dissolving 3 g of a yeast extract, 3 g of a malt extract, 5 g of peptone, 10 g of glucose, and 50 g of glycerol in 1 L of deionized water.
   MEL production medium: prepared by dissolving 5 g of a yeast extract, 3 g of sodium nitrate, 0.3 g of potassium dihydrogen phosphate, 0.3 g of magnesium sulfate hemihydrate, and 20 g of glycerol in 1 L of deionized water.
2. Investigation of Extraction Solvent for Monoacyl MEL
2-1. Culture of Monoacyl-MEL-Producing Strain A monoacyl-MEL-producing strain was cultured with shaking in 2 mL of a YM medium containing glycerol at 25° C. for 2 days to obtain a pre-culture broth. Subsequently, 1 mL of the pre-culture broth was inoculated into 20 mL of a MEL production medium (containing 0.005% Triton X-100) supplemented with 3% olive oil, and cultured with shaking at 25° C. for 7 days. On the third day of the culture, 2% olive oil was added (total amount of oil added: 5%).
2-2. Extraction of Monoacyl MEL The monoacyl MEL extraction from the culture broth was tested using various solvents (ethyl acetate, methanol, ethanol, and acetone). The culture broth obtained in 2-1 above was centrifuged at 3,000 rpm, and the culture supernatant was collected. Ethyl acetate was directly added to the collected supernatant. The resulting ethyl acetate layer containing monoacyl MELs was collected, and the obtained layer was used as an ethyl acetate extract. In the methanol extraction, the supernatant that was collected first was frozen at −20° C. and then freeze-dried. Methanol was added to the dried supernatant, stirred by vortexing, and then allowed to stand at room temperature overnight. After being allowed to stand, the resulting mixture was allowed to stand, and the methanol layer was collected and filtered through a 0.45 μm filter. The obtained filtrate was used as a methanol extract. Extraction with ethanol and extraction with acetone were also performed in the same manner as the extraction using methanol.
2-3. Evaluation of the Amount of Monoacyl MEL in Extracts The amount of monoacyl MEL in each solvent extract was analyzed by thin-layer chromatography (TLC). The composition of the developing solvent was chloroform:methanol: 12% ammonia water=55:25:2. A 2% anthrone sulfate reagent was sprayed over TLC plates after development, and the developed plates were heated at 95° C. for 5 minutes to detect spots of monoacyl MEL.

Figure 3:
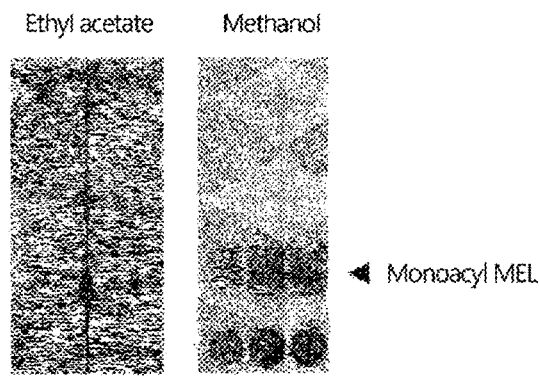
FIG. 3 shows the thin-layer chromatography evaluation results of monoacyl MELs extracted with ethyl acetate and methanol.

As shown in FIG. 3, the amount of monoacyl MELs extracted with ethyl acetate was confirmed to be smaller than the amount extracted with methanol. The two separate spots of monoacyl MELs in the methanol extract are presumably attributable to the influence of moisture in the solvent.

Figure 4:
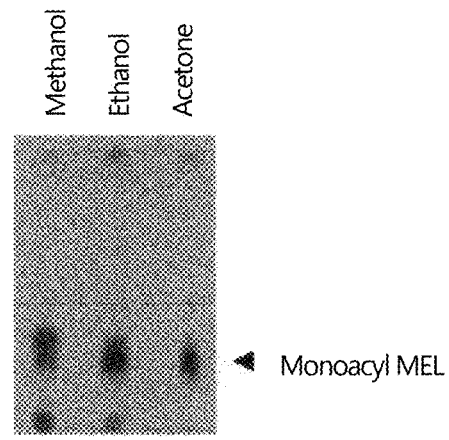
FIG. 4 shows the results of thin-layer chromatography evaluation of monoacyl MELs extracted with methanol, ethanol, and acetone.

FIG. 4 shows the results of extraction with ethanol and extraction with acetone that were performed in the same manner. As with the extraction with methanol, extraction with ethanol and extraction with acetone were confirmed to be able to more efficiently extract monoacyl MEL than the extraction with ethyl acetate. In particular, in acetone extraction, highly hydrophilic impurities, which were detected at the origin in methanol or ethanol extraction, were hardly detected, and only monoacyl MEL was confirmed to be detectable. Further, unlike methanol or ethanol extraction, a single spot of monoacyl MEL was detected in acetone extraction.
3. Evaluation of Amount of Monoacyl MEL Production
3-1. Culture of Monoacyl-MEL-Producing Strain A monoacyl-MEL-producing strain was cultured with shaking in 2 mL of a YM medium with glycerol at 25° C. for 2 days to obtain a pre-culture broth. Subsequently, 1 mL of the pre-culture broth was inoculated into 20 mL of a medium containing 3% olive oil, and cultured with shaking at 25° C. for 7 days. On the third day of culturing, 2% olive oil was added (total amount of oil added: 5%). As the MEL production media, a medium without a surfactant and media containing a surfactant (MEL-B, Tween 20, Triton X-100, or BRIJ35) at a concentration of 0.01% or 0.1% were used.
3-2. Extraction of Monoacyl MEL The culture broth obtained in section 3-1 above was centrifuged at 3,000 rpm, and the culture supernatant was collected. The collected supernatant was frozen at −20° C. and then freeze-dried. Acetone was added to the dried supernatant, and the resulting mixture was stirred by vortexing and then allowed to stand at room temperature overnight. Thereafter, the acetone layer was collected and filtered through a 0.45 µm filter. The obtained filtrate was used as an acetone extract.

3-3. Evaluation of the Amount of Monoacyl MEL in the Extracts

The amount of monoacyl MELs in each acetone extract was analyzed by thin-layer chromatography (TLC). The composition of the developing solvent was chloroform:methanol:12% ammonia water=55:25:2. A 2% anthrone sulfate reagent was sprayed over TLC plates after development, and the developed TLC plates were heated at 95° C. for 5 minutes to detect spots of monoacyl MELs.

3-4. Monoacyl MEL Production without Surfactant Addition

Figure 5:
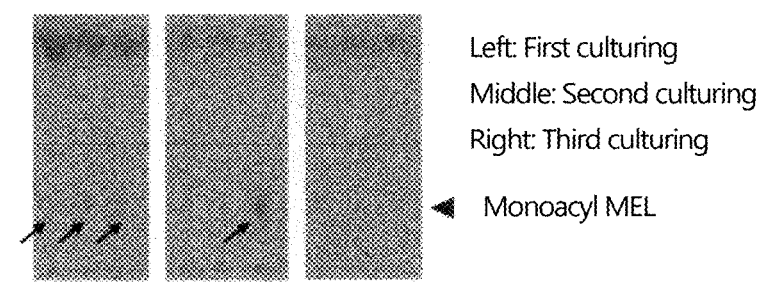
FIG. 5 shows the thin-layer chromatography evaluation results of the amount of monoacyl MEL production when monoacyl MEL-producing yeast was cultured in a surfactant-free medium.

FIG. 5 shows the results of subjecting a monoacyl-MEL-producing strain to culturing a total of 3 times in a MEL production medium without a surfactant (n=3 for each culturing). The TLC plates on the left, middle, and right in FIG. 5 show the first, second, and third culturing results, respectively. As shown in FIG. 5, the results confirmed that when culture was performed without surfactant addition, either no monoacyl MEL was produced (third culturing), or only a very small amount of monoacyl MELs was produced (first culturing), if any. Even when three samples (n=3) were subjected to each culturing, monoacyl MELs were detected from only one sample in a case (in the second culturing); the results thus confirmed that the production is unstable. The amount of cell growth was 21.9±2.8 g/L on average for a total of culturing 3 times.

3-5. Production of Monoacyl MEL with MEL-B Addition

Figure 6:
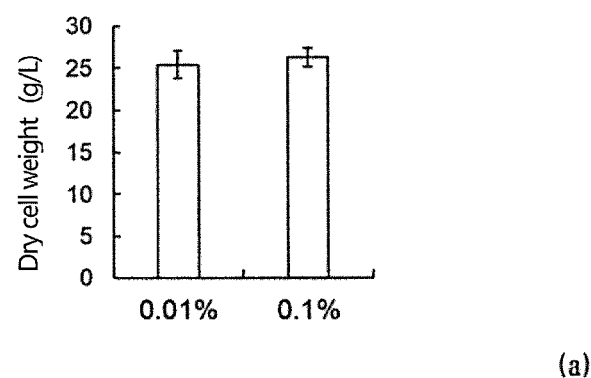
FIG. 6 shows the amount of cell growth (a) and the result of thin-layer chromatography evaluation of the amount of monoacyl MEL production (b) when monoacyl MEL-producing yeast was cultured in a medium containing MEL-B.
Figure 6:
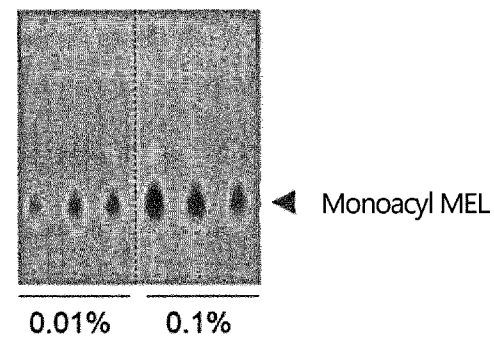

FIG. 6 shows the results of culturing a monoacyl-MEL-producing strain in a MEL production medium containing MEL-B. FIG. 6(a) shows the amount of cell growth; and FIG. 6(b) shows the results of TLC analysis. As shown in FIG. 6, the results confirmed that the addition of 0.01% MEL-B or 0.1% MEL-B significantly increases the amount of monoacyl MEL production as compared to the amount obtained without adding MEL-B, and that monoacyl MELs were stably produced in all cultures. The amount of cell growth was also larger than the amount obtained without adding MEL-B.

3-6. Production of Monoacyl MEL with Tween 20 Addition

Figure 7:
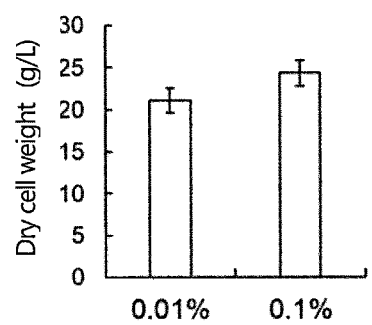
FIG. 7 shows the amount of cell growth (a) and the result of thin-layer chromatography evaluation of the amount of monoacyl MEL production (b) when monoacyl MEL-producing yeast was cultured in a medium containing Tween 20.
Figure 7:
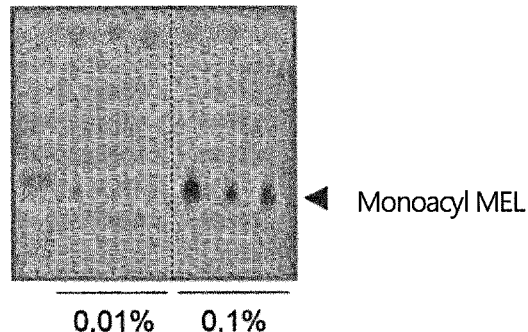

FIG. 7 shows the results of culturing a monoacyl-MEL-producing strain in a MEL production medium containing Tween 20. FIG. 7(a) shows the amount of cell growth; and FIG. 7(b) shows the results of TLC analysis. As shown in FIG. 7, the results confirmed that the addition of Tween 20 increases the amount of monoacyl MEL production as compared to the amount obtained without adding Tween 20, and that monoacyl MELs were stably produced in all cultures. The amount of cell growth was also larger than the amount obtained without adding Tween 20.

3-7. Production of Monoacyl MEL with Triton X-100 Addition

Figure 8:
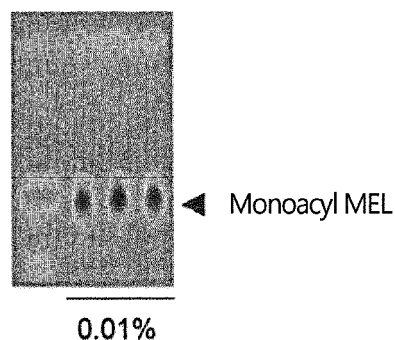
FIG. 8 shows the result of thin-layer chromatography evaluation of the amount of monoacyl MEL production when monoacyl MEL-producing yeast was cultured in a medium containing Triton X-100.

FIG. 8 shows the results of culturing a monoacyl-MEL-producing strain in a MEL production medium containing TritonX-100. As shown in FIG. 8, the results confirmed that the addition of 0.01% Triton X-100 significantly increased the amount of monoacyl MEL production as compared to the amount obtained without adding Triton X-100, and that monoacyl MELs were stably produced in all cultures. The amount of cell growth was 25.0±0.4 g/L, which was larger than the amount obtained without adding Triton X-100.

3-8. Production of Monoacyl MEL with BRIJ35 Addition

Figure 9:
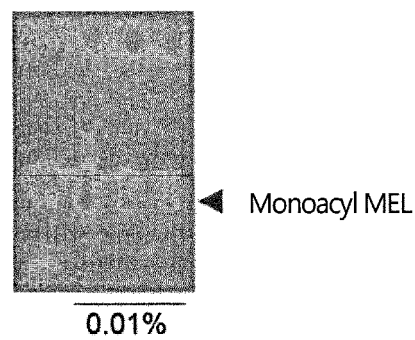
FIG. 9 shows the result of thin-layer chromatography evaluation of the amount of monoacyl MEL production when monoacyl MEL-producing yeast was cultured in a medium containing BRIJ35.

FIG. 9 shows the results of culturing a monoacyl-MEL-producing strain in a MEL production medium containing BRIJ35. As shown in FIG. 9, the results confirmed that the addition of 0.01% BRIJ35 increases the amount of monoacyl MEL production as compared to the amount obtained without adding BRIJ35, and that monoacyl MELs were stably produced in all cultures. The amount of cell growth was 20.6±0.4 g/L.

3-9. Production of Monoacyl MEL with Sodium Laurate Addition

Using a MEL production medium containing 0.01% sodium laurate, which is an anionic surfactant, a monoacyl MEL-producing strain was cultured in the same manner as in the above test. The results confirmed that the amount of monoacyl MEL production increases and that the production of monoacyl MEL is stabilized as compared to the case without using the surfactant.

It is presumed that the addition of MEL-B to the medium promoted emulsification and dispersion of the raw material fat and/or oil, thus resulting in the promotion of monoacyl MEL production.

The invention claimed is:

1. A method for producing a monoacyl MEL, comprising culturing a microorganism capable of producing the monoacyl MEL in the presence of a surfactant and producing the monoacyl MEL.

2. The method according to claim 1, wherein the surfactant is a nonionic surfactant.

3. The method according to claim 1, wherein the microorganism is a microorganism that belongs to the genus *Pseudozyma*.

4. The method according to claim 1, wherein the microorganism is deficient in a gene encoding a mannose acyltransferase.

5. The method according to claim 1, further comprising extracting the monoacyl MEL using at least one member selected from the group consisting of methanol, ethanol, acetone, and mixtures thereof.

6. The method according to claim 2, wherein the microorganism is a microorganism that belongs to the genus *Pseudozyma*.

7. The method according to claim 6, wherein the microorganism is deficient in a gene encoding a mannose acyltransferase.

8. The method according to claim 7, further comprising extracting the monoacyl MEL using at least one member selected from the group consisting of methanol, ethanol, acetone, and mixtures thereof.

* * * * *

SEQUENCE LISTING

```
<160> NUMBER OF SEQ ID NOS: 6

<210> SEQ ID NO 1
<211> LENGTH: 1745
<212> TYPE: DNA
<213> ORGANISM: Pseudozyma antarctica

<400> SEQUENCE: 1
atgacgacgg aagacaatca gcgttggagc caagtctctc ctgacctcgc aaagaggccg      60
ctcgtcggcg tggagaaggt gctcaactac accgaatact atcagaatgg aaacgtacgt     120
gtataagtcc ttacccgtcg tagcctcgac gagcttgcat gctgataatg acccacactc     180
gtctccgtcg tggtacgaac gtacagttcc aactcacgat cgctctcctc ttcgagacaa     240
gcgtcgcatc agagactctg tgcgagcgct tcccccttgc cctctggtcc gttcgctcca     300
agctgccaga gctcggaacc tcgacggtaa gcaacgacca gagcgcggag ctcgacctcg     360
atcatgcgct gtggcagccg attcgatcgc tggaacaggc tcaacagtgg cttgatgaca     420
```

| | |
|---|---|
| ccggcgttat cgtcaacgac ggcacctcgg tccagcagat ggtcgatcgc ctctccaacc | 480 |
| gtcgcatcga gccgattggc aagcagttcc gcgtgtacct agtgtgtgat ccgctttacg | 540 |
| gcgctccggg tctcatcgtc aatgcctctc acgtcctcaa cggccaccgg gcgctcttcc | 600 |
| agggcgagtc gatcttcaag gctctcctga gcccacgcat ctcggacgcg accaggcaga | 660 |
| acccggatgc caaggctgcg ctggcggcca tcttcaagcc agaagagctg aacgaagcgc | 720 |
| ttccgaagct tccacagagc ctcaacaccg cctatgccga caattccaa ccgggcgctc | 780 |
| cggagatcga agcaggcttc cacaaggtgg gtgagaagct ctccaacggt gcgcagccgt | 840 |
| cgatcggcat cctcgattc cagattccaa gcgcgaagcc tgcattctca ctgggaagcc | 900 |
| tcgacgggac gccgatgtcg atgctcaacc tacgatctcg gatcaacgcc gccgacaatc | 960 |
| agagtctcaa acgcgcgtgc aagaaatacg gtgcgagcgt accttcgctc gtctatgcgt | 1020 |
| gcattgtgaa cagcatcgat cgacactgcg gatcaagctc aagcgaggct gtgctgggtg | 1080 |
| ccaaccttgc gtactctgcg catgcgagcc gttggatgcc ggccgagacg tttgaggagc | 1140 |
| gctcgccggt caacatggcg attgtgcttg ggtcgggata cctgtctccc gaggagctgc | 1200 |
| agccaggaca gcgcggacgc aacctcggcg aggcgggact ctttgcgctc gcacgcacga | 1260 |
| tccgcaagaa gcaagacgac tttctcgaca caccgcacat catcggagcc atgtccgatc | 1320 |
| ttggagagca ggtttcgtcg cagcttgccg aagtggccga gccaacgc gaagcaggga | 1380 |
| ctgatgcgcg cgtagcgctg tcggaaaact cgccgctcgt ctgcccccg acactgactt | 1440 |
| cgcagggagt cattaccgtc aagcgattct acacggctca aggtgcttcc gacgagctgc | 1500 |
| atctggagca gcctgccgac gagcatctgg agttttcga catctgcacg gcggcagaa | 1560 |
| ctacggatgc ctcggtgtgc tttgcgatgt tcacgcacgt tggagctttg acgctgcagg | 1620 |
| cgcactttga ctcgcacttt ttcgacgccc agcttgtccg caacatcctg gacgacgtgg | 1680 |
| tttcgcagct tggctcggcc gctgcctctg ctagtctcac cagccaagac caagccaagc | 1740 |
| tctag | 1745 |

<210> SEQ ID NO 2
<211> LENGTH: 1659
<212> TYPE: DNA
<213> ORGANISM: Pseudozyma antarctica

<400> SEQUENCE: 2

| | |
|---|---|
| atgacgacgg acgaaaatca gccttggagc caagtctctc cggacctcgc caagaggccg | 60 |
| ctcgtcggtg tggagaaggt gctcaactac acagaatact accagaacgg aaacttccaa | 120 |
| ctcacgattg ctctgctctt cgagacaggc attgcatcag agactctgtg cgagcgctta | 180 |
| ccacttgccc tttggtctgt tcgcactcga ctgccagagc tcggaacctg acagtgacc | 240 |
| aatgaccaga gcgcggagct tgacctcgat catgcgctgt ggcagcccat ccgatcgctc | 300 |
| gagcaggctc aacagtggct tcacgacacc gccgtcgtcg tcaacgacgg cactactgtt | 360 |
| cagcagatgg tcgatcgcct ttctaaccgt cgcatcgagc cggtcggcaa gcagttccac | 420 |
| gtctacctcg tttgcgatcc gctctacgga gcttccggtc tcatcgtcaa tgcctctcac | 480 |
| gtgctcaacg gccatcgggc gctcttccag ggcgagttga ttttcgaggc gctcctcaac | 540 |
| ccgcgcatct cggacgcgat caggcagcat caggatgctg gggctgcgct cgcggccatg | 600 |
| ttcaagcccg aagagctgtc cgaatcgctt gcgaagcttc gcagagcct caacaccgcc | 660 |
| tatgcggaca agttccagcc gggcgcatcg agatcgcag cgggcttcca caaggtgggt | 720 |
| gagaagctgg ccaacggtgc tcagccgtcg atcggcattc ctcgattcga agcacccagc | 780 |

```
gcaaagcctg catactctct cggcacctac gatggtgtgc acatgtcgat gctcaacttg    840
cgatcgcgaa tcaaggcggc ggataatcag aacctcaagc gcgcctgcaa gaagaacgga    900
gcgagcgtgc cttcgctcgt gtatgcatgc attgtgaaca gcattgatcg acgctgcggg    960
tcgagcacgg gctctgatgg cgctgcgctg ggtgccaacc ttgcgtactc tgcgcatgca    1020
agtcgatgga tgccggcgga gacgttcatg gagcgctcgc cagtcaacat ggcgattgtg    1080
ctcggttcgg gatacttgtc tcccgaagag ctgcagccag acagcgcgg aagcaacctg     1140
gacgaggcag gactctttgc actcgcgcgc acgattcgcc aaaagcaaga cgactttctc    1200
gacacaccgc acatcattgg tgccatgccg gatctcggag agcaagtttc gtcgcagctt    1260
gcccaagcgg ccgagcgtca acgacaagca gggacggact ggcgcttagc actttcggaa    1320
acctcgccgt tggtctgccc tcctacactg acttcgcagg gagtcatccc cgtcaagcga    1380
ttctacacgg cccagggtgc ctccaacaag cttcagctgg agcagcctgc ggaggagtac    1440
ctcgagtttg tcgacatttg ctcgggtggt aggactacag atgcctcggt gtgctttgcc    1500
atgttcaccc acgccggtgc tttgacgctg caggcccact ttgactcgca ctttttcgac    1560
gccaagctcg tccgcagcat cttggacgat gtagtgtcgc agctgcgtgc tgccgctgca    1620
tctgcaagtc tcaccagccc agaccaagcc aagctctag                           1659

<210> SEQ ID NO 3
<211> LENGTH: 1662
<212> TYPE: DNA
<213> ORGANISM: Pseudozyma hubeiensis

<400> SEQUENCE: 3
atgctcaact acgccgagta ctatcagaat ggcaatgtga gtacagcagt cagccttcgc     60
cgttcagtga atcttcgttc tggagctgat ggattcgtaa ttgctggcct gactgtacag    120
ttccaattgt cggtcaccct caactttgag accaacgtct cggcgcagaa gcttcgacaa    180
cgctttggct tggcggtctg ggccgtcaga ggcttttttgc cagagctcgg catgtggacg    240
acaaccacgt ccaccgatgg ctctctggat cttgaccacg tcaccttcac agcattgcag    300
accgctgacg aggctcaaga atggatccaa gacaccgcca tcgtcgtcga cgatggtacc    360
accactgagg agctgatgaa ctacaactcg aaccatcgca tcgagcctcc tggaaagcaa    420
ttccgtgtct atctcgttct gaatccacgt cgaggatcgc cctcgatcgt gttgaatgcc    480
tctcacgtcc tcaacggtca tcgagctcat gttcaatgct gcgctatctt ggaagcaatg    540
atgagtgaca agctcgtttc gctcctagag gcaactccag accgcgtct ggcacttggg    600
gccctctttg cccccgagga tgtatcgaag gttcttggca agctgcccat cagcctcgat    660
accgcctacc aggaacgatt caaaccgacg gaaaccgacc tcgatgtagg catggagaag    720
cttggcgagc ggctcaccaa cagcgcgctg ccgacgatcg gcgtccctcg cttcgaatct    780
ccagcaaaga gccccgagta ttcgctcggc aatgcccacg ccaaccgat gaccatgctc     840
aatctgaaga gggagatgga tttcaacgag tatcgcaaag tgagacaggc gcacaagaag    900
ctcggcatca ccgttccctc gttcgtctac gcgtgcatcg tcaacagcat tgatcgacgc    960
tgcaaggcga gcacggccca agacgacgag acgccagggg cacatttagc ctactctgcg    1020
cacgccagtc gctggttccc cgccgagaca ttcatgagtc gctctcccgt caacatggcc    1080
atcgtccccg gatccggcta catttctcca cacgagcttc gatcggagca acgcgggcgt    1140
gatctaagct tgaatgagct gatcgcgctg tcaaagacga tccgacaaag gcaagaggca    1200
```

```
tttctcgcca gcccgcatat cgtgtctacg ttggagcagg tggctgacga agtctcccgg    1260
aacatcgcag agacgccag caagcagcaa caggccggca cagatccgct cgtggctctc    1320
tgtcaaaact ctcccgccat ctgtccgcct accttgacat cgcagggtga caacgtcttc    1380
aaccggctct tcacagccaa gggtggctcg ttggaaggca ggccagccaa cctcgaggga    1440
gactacatct acgtcaacag gggctatatc agcggtcgaa ccacggatgc caccgtctgc    1500
ttcgcgctgc tcggtttcgg tggcgtgttg tcgcttgcag gtcactttga ctcgcgcttc    1560
ttcgacgcca agctcgtcga tgcaattctg gatgacgtgt ggaagaattt gcgagcaatc    1620
gctgcaaccg tcgccgaaga agagcgcgag gccaagctct aa                      1662

<210> SEQ ID NO 4
<211> LENGTH: 1748
<212> TYPE: DNA
<213> ORGANISM: Pseudozyma tsukubaensis

<400> SEQUENCE: 4
atgctaggag atcaagtttg gaaggaggtc tcttccaata ctcttcgcag acccttgatc      60
ggcgtcgaga agatgatcaa ctatgccgaa tactatcaaa atggaaacgt gagtctccgc     120
tttcaccccc tccgaccgct cgagtcaaac gtatatgctg acctgccatt gttctgccat     180
gtgaactcca accatttact ctgcagtttc aattgacgat tgcattgagc ttggacacca     240
atctgtcagc cgacaagatg caagagcgac tcggtctggc tctctggacc gtaagaggct     300
atctacccga gcttggcacc tggactgtcg gctcttcgca ggattcgact ttagatctcg     360
atcatgtcac tttcaaggct atccagacag tcgaagaggc acaagaatgg atcgaggaca     420
ccgctattct cgtggacgaa ggtacaacag tatcagaaat ggtcgatctc ctctcgaaca     480
agcgaatcga gccggttggc aagcagtttc gcgcctatct cgtgtctcaa ccgcgacacg     540
gcaagccagc attggtcatg aatgcttctc atacgctaaa tggtcaccgc atgctcttcc     600
aaggttctgc tatcttgcaa gccctcgtcg atgccagact caccgctctg gtagccagca     660
gcaacagctc tcgtgaggcg ctcgaggccg tcttcgtgcc cgaagacatc tcgcgtttgg     720
cacgcaagct gcctcagagt ctcaacaccc ctacgccga caagttccga cctgatgagg      780
ctgacgtcga agcgggcttc gcaaaactcg gagagcgcat tctgaacagc actcagccta     840
ctctcggcat cccgcggttc tcaactcctt ctcaaaatcc acaatatacg ctcggttcgg     900
ccaacggtca acctctgacc atgctcaacc ttcgacggca atcggtgtc acggaacacc      960 gcatgcttca tcgcgcgttc aagaagcggg gatccagcct accctcgttc acctatgcct    1020
gtattgtcaa cagcatcgac cgacgttgca aggccagcac ttccgaggca gacgaggcac    1080
caggtgccaa ccttgtttac tcggcacatg ctagtcgatg gttcccagca gagactttta    1140
tgtcgcgctc gcctgtcaac atggctattg ttccaggatc cggttatgtc gcgcccgaag    1200
agctgcgatc taagcagcgt ggtcgcgatc tcaacgaaag cgagctcttt gcccttgcca    1260
agaccattcg agcgaagcag gagcagtatc tcgaatctcc gcatatcatc tcctacactg    1320
cacaggtcgg cgatgacatc gcagctgcca tggctgagac cgccaacaag cagcgtcaag    1380
caggaaccga tccgtacgtt gcactgtccg aaaactctcc tgctatctgc cccctacac     1440 tgacttcgca aggtgaagtt cccatcaaga acctgtacac gcccgagggg cttcctttg     1500 atcccaagcc gaagcaaccc gaatacgagt acatctactt cggtgaaggt ctgcttggtg    1560
gcagaacgac cgatgcttcc gtctgctttg ccttatggag tctcgctggc attttgacgc    1620
ttcaagctca cttttgattca cgcttctttg acgctcaggt catcgatacc attctcgatg    1680
```

| | |
|---|---|
| atgttgttct tcagcttcgc cgttctgcag ctagtgccgt cgatgaagct cctgaggcca | 1740 |
| agctttag | 1748 |

<210> SEQ ID NO 5
<211> LENGTH: 1748
<212> TYPE: DNA
<213> ORGANISM: Pseudozyma tsukubaensis

<400> SEQUENCE: 5

| | |
|---|---|
| atgctaggag atcaagtttg aaggaggtc tcttccaata ctcttcgcag acccttgatc | 60 |
| ggcgtcgaga agatgatcaa ctatgccgaa tactatcaaa atggaaacgt gagtctccgc | 120 |
| tttcaccccc tccgaccgct cgagtcaaac gtatatgctg acctgccatt gttctgccat | 180 |
| gtgaactcca accatttact ctgcagtttc aattgacgat tgcattgagc ttggacacca | 240 |
| atctgtcagc cgacaagatg caagagcgac tcggtctggc tctctggacc gtaagaggct | 300 |
| atctacccga gcttggcacc tggactgtcg gctcttcgca ggattcgact ttagatctcg | 360 |
| atcatgtcac tttcaaggct atccagacag tcgaagaggc acaagaatgg atcgaggaca | 420 |
| ccgctattct cgtggacgaa ggtacaacag tatcagaaat ggtcgatctc ctctcgaaca | 480 |
| agcgaatcga gccggttggc aagcagtttc gcgcctatct cgtgtctcaa ccgcgacacg | 540 |
| gcaagccagc attggtcatg aatgcttctc atacgctaaa tggtcaccgc atgctcttcc | 600 |
| aaggttctgc tatcttgcaa gccctcgtcg atgccagact caccgctctg gtagccagca | 660 |
| gcaacagctc tcgtgaggcg ctcgaggccg tcttcgtgcc cgaagacatc tcgcgtttgg | 720 |
| cacgcaagct gcctcagagt ctcaacaccg cctacgccga caagttccga cctgatgagg | 780 |
| ctgacgtcga agcgggcttc gcaaaaactcg gagagcgcat tctgaacagc actcagccta | 840 |
| ctctcggcat cccgcggttc tcaactcctt ctcaaaatcc acaatatacg ctcggttcgg | 900 |
| ccaacggtca acctctgacc atgctcaacc ttcgacggca aatcggtgtc acggaacacc | 960 |
| gcatgcttca tcgcgcgttc aagaagcggg gatccagcct accctcgttc acctatgcct | 1020 |
| gtattgtcaa cagcatcgac cgacgttgca aggccagcac ttccgaggca gacgaggcac | 1080 |
| caggtgccaa ccttgtttac tcggcacatg ctagtcgatg gttcccagca gagactttta | 1140 |
| tgtcgcgctc gcctgtcaac atggctattg ttccaggatc cggttatgtc gcgcccgaag | 1200 |
| agctgcgatc taagcagcgt ggtcgcgatc tcaacgaaag cgagctcttt gcccttgcca | 1260 |
| agaccattcg agcgaagcag gagcagtatc tcgaatctcc gcatatcatc tcctacactg | 1320 |
| cacaggtcgg cgatgacatc gcagctgcca tggctgagac cgccaacaag cagcgtcaag | 1380 |
| caggaaccga tccgtacgtt gcactgtccg aaaactctcc tgctatctgc cccctacac | 1440 |
| tgacttcgca aggtgaagtt cccatcaaga acctgtacac gcccgagggg cttcctttg | 1500 |
| atcccaagcc gaagcaaccc gaatacgagt acatctactt cggtgaaggt ctgcttggtg | 1560 |
| gcagaacgac cgatgcttcc gtctgctttg cctatggag tctcgctggc attttgacgc | 1620 |
| ttcaagctca ctttgattca cgcttctttg acgctcaggt catcgatacc attctcgatg | 1680 |
| atgttgttct tcagcttcgc cgttctgcag ctagtgccgt cgatgaagct cctgaggcca | 1740 |
| agctttag | 1748 |

<210> SEQ ID NO 6
<211> LENGTH: 1751
<212> TYPE: DNA
<213> ORGANISM: Pseudozyma aphidis

```
<400> SEQUENCE: 6
atgtccacgg acgacaatca gcgttggagc caagtctctc cggacctcgc caagaggccg          60
ctcgtcggtg tcgagaaggt gctcaactac acagaacact atcaagacgg aaatgtacgt         120
gcatacgtcc caacagtcgc gagctagacg atcgtgcata ctgattttga cccacgatcg         180
attttgtgcc tacatcgacc ttgcagttcc aactcacgat cgctctcctc ttcgagacaa         240
gcattgcatc agagactctg tgcgaacgct tcccacttgc cctttggtcc gttcgctctc         300
agctgccaga gctcgggacc tggacagtga ccaacgacca gagtgcggag cttgacctcg         360
atcatgcgct gtggcagccc atccgatcgc tcgaacaggc tcaacagtgg cttcatgaca         420
ccgccgtcgt cgccaacgat ggcaccactg ttcagcagat ggtcgatcgc ctttctaacc         480
gtcgcatcga gccggtcggc aagcagttcc gcgtatacct cgtttgcgat ccgctctacg         540
gagctcccgg tctcattgtc aatgcttccc acgtcctcaa cggccatcgg gcgctcttcc         600
agggcgagat gatcttccag gcgcttctcg acccgcgcat caccggaacc ttgaggcagc         660
acccagactc cacgtctgcg ctcgcggcca tcttcaagcc tgaagagctg tccgaatcgc         720
ttccgaagct tccgcagagc ctcaacaccg cctatgcgga caagttccag ccgggcgcat         780
cggagatcgc agcgggcttc cataaggttg gtgagaagct ggccaacggt gctcagccgt         840
cgatcggcat tcctcgattc caagttccaa gcggaacgcc tgcattttct ctgggaatgc         900
acgacggcac gccaatgtcg atgctcaacc tgcgatctcg aatcaaggcg gcggacaatc         960
agagccttaa gcgcgcctgc aagaagtacg gagcgagcgt accttcgctc gtgtatgcat        1020
gcattgtgaa cagcatcgat cgacactgcg ggtcgagcac gggctctgat ggcgctgcgc        1080
tgggtgccaa ccttgcctac tctgcgcatg caagtcgatg gatgccggcg gagacgttca        1140
tggagcgctc gccagtcaac atggcgattg tgctcggatc gggataccte tctcccgagg        1200
agctgcatcc agggcagcgc ggaagcgacc tgggcgaggc ggggcttttt gcactcgcgc        1260
gcacgattcg ccaaaagcaa gacgactttc tcgacacacc acacatcatt ggtgccatgc        1320
cggatctcgg agagcaggtt tcgtcgcagc ttgccgaagc ggccgagcgc caacgagaag        1380
cagggactga ctggcgctta gcactctcgg aaaactcgcc ggcggtctgc cctcctacac        1440
taacttcgca gggagtcatc cccgtcaagc gattctacac ggcccagggt gcctcgaaca        1500
agctgcagct ggggcagcct acggaggagt acctcgagtt tgtcgacatt tgctcgggtg        1560
gcagaaccac ggatgcctcg gtgtgctttg ccatgttcac ccacgccggt gctttgacgc        1620
tgcaggcaca ctttgactcg catttttcg acgccaagct cgtccgcaac atcttggacg        1680
atgtagtgtc gcagctgcgt gctgctgctg catctgcaag cctcaccagt cttgaccaag        1740
ccaagctcta g                                                              1751
```